(12) United States Patent
Kobilka et al.

(10) Patent No.: US 11,072,744 B2
(45) Date of Patent: Jul. 27, 2021

(54) COVALENTLY-BOUND POLYBROMOCYCLODODECANE FLAME RETARDANTS

(71) Applicant: International Business Machines Corporation, Armonk, NY (US)

(72) Inventors: Brandon M. Kobilka, Tucson, AZ (US); Joseph Kuczynski, North Port, FL (US); Jason T. Wertz, Pleasant Valley, NY (US); Scott B. King, Rochester, MN (US)

(73) Assignee: International Business Machines Corporation, Armonk, NY (US)

( * ) Notice: Subject to any disclaimer, the term of this patent is extended or adjusted under 35 U.S.C. 154(b) by 0 days.

(21) Appl. No.: 16/157,221

(22) Filed: Oct. 11, 2018

(65) Prior Publication Data
US 2020/0115633 A1  Apr. 16, 2020

(51) Int. Cl.
| C09K 21/08 | (2006.01) |
| C07C 23/02 | (2006.01) |
| C08J 3/24  | (2006.01) |
| C08K 5/02  | (2006.01) |
| C08K 5/37  | (2006.01) |
| C08K 5/03  | (2006.01) |
| H05K 1/03  | (2006.01) |
| C08K 5/10  | (2006.01) |

(52) U.S. Cl.
CPC ............... *C09K 21/08* (2013.01); *C07C 23/02* (2013.01); *C08J 3/24* (2013.01); *C08K 5/02* (2013.01); *C08K 5/03* (2013.01); *C08K 5/10* (2013.01); *C08K 5/37* (2013.01); *H05K 1/0326* (2013.01); *H05K 1/0333* (2013.01); *H05K 2201/012* (2013.01)

(58) Field of Classification Search
CPC .................................. C09K 21/08; C07C 23/02
See application file for complete search history.

(56) References Cited

U.S. PATENT DOCUMENTS

| 4,783,563 A | 11/1988 | Taniuchi et al. |
| 4,918,253 A | 4/1990 | Hermolin et al. |
| 5,693,410 A * | 12/1997 | Malhotra ............... B41M 5/52 |
| | | 428/32.13 |
| 6,506,952 B2 | 1/2003 | Kendall |
| 10,174,140 B2 | 1/2019 | Lai et al. |
| 2002/0045783 A1 | 4/2002 | Kendall |
| 2008/0027160 A1 | 1/2008 | Zingg et al. |
| 2020/0115634 A1 | 4/2020 | Inagaki et al. |

FOREIGN PATENT DOCUMENTS

| CN | 1128748 A | 8/1996 |
| CN | 106146254 A | 11/2016 |

OTHER PUBLICATIONS

High-resolution mass spectrometry provides novel insights into products of human metabolism of organophosphate and brominated flame retardants. Anal Bioannal Chem (2015) 407:1871-1883 (Year: 2015).*
Mo et al., "Bioaccumulation of polybrominated diphenyl ethers, decabromodiphenyl ethane, and 1,2-bis(2,4,6-tribromophenoxy)ethane flame retardants in kingfishers (Alcedo atthis) from an electronic waste-recycling site in South China." Environ Toxicol Chem., Sep. 2012;31(9):2153-8, doi: 10.1002/etc.1929, Epub Jul. 20, 2012, Abstract Only, 2 pages.
SciFinder search results for synthesis of brominated flame retardants, 8 pages.
Sun et al., "Synthesis of Br7—Br9 hydroxylatedlmethoxylated polybrominated diphenyl ethers (OH/MeO—PBDEs) and analyses on mass spectra and GC data of the MeO-PBDEs," Chemosphere 92 (2013) 286-292, Elsevier.
Teclechiel et al., "Synthesis of polybrominated diphenyl ethers via symmetrical tetra- and hexabrominated diphenyliodonium salts," Chemosphere 74 (2008) 421-427, Elsevier.

* cited by examiner

*Primary Examiner* — Wenwen Cai
(74) *Attorney, Agent, or Firm* — Kelsey M. Skodje (57) ABSTRACT

A polybrominated flame-retardant compound, a process for forming a flame-retardant material, and an article of manufacture are disclosed. The polybrominated flame-retardant compound includes a cyclododecane moiety, at least two bromo groups, and at least one substituent having a reactive functional group. The process includes forming a polybromocyclododecane (PBCD) compound having at least one reactive functional group and incorporating the PBCD compound into a polymer in a process that includes covalent binding of the PBCD compound. The article of manufacture includes a flame-retardant material that comprises a polymer with a covalently-bound PBCD compound.

20 Claims, 11 Drawing Sheets

NaBH₄,
THF

FIG. 7

COVALENTLY-BOUND POLYBROMOCYCLODODECANE FLAME RETARDANTS

BACKGROUND

The present disclosure relates to brominated flame retardants and, more specifically, to polybromocyclododecane compounds that can covalently bind to polymers.

Brominated flame retardants (BFRs) are organobromide compounds that can be added to a variety of plastics, resins, synthetic fibers, insulation foams, and other materials in order to provide flame retardancy. In the electronics industry, BFRs are often used in printed circuit boards, connectors, plastic covers, and electrical cables. Examples of BFRs that can be blended with polymeric materials include polybrominated diphenyl ethers, tetrabromobisphenol A, hexabromocyclododecane, and other brominated cyclohydrocarbons.

SUMMARY

Various embodiments are directed to a brominated flame-retardant compound that includes a cyclododecane moiety, at least two bromo groups, and at least one substituent having a reactive functional group. In some embodiments, the at least two bromo groups are bound to the cyclododecane moiety, though at least one of the bromo groups can also be bound to the substituent. Examples of reactive functional groups that can be part of the substituent can include a hydroxyl group, an epoxide group, a vinyl group, an acryloyl group, a methacryloyl group, a propylene carbonate group, an oxalate group, a carboxylic acid group, an amine group, and an amide group. The substituent can also include an allyl group, a benzyl moiety, or a thioether linkage. Further, the substituent can be linked to the cyclododecadiene moiety by an oxygen atom linker or an ester linker.

Additional embodiments are directed to a process of forming a flame-retardant polymer. The process includes providing a polybromocyclododecane compound having at least one reactive functional group and incorporating the polybromocyclododecane compound to the polymer through covalent binding. The polymer can be a polystyrene, an epoxide resin, a polyhydroxyurethane, a polycarbonate, a polyester, a polyacrylate, a polyimide, a polyamide, a polyurea, or a poly(vinyl-ester). The process of forming the functionalized polybromocyclododecane compound can also include selecting a substituent having the reactive functional group, providing a compound having the selected substituent, and reacting the compound having the selected substituent with a brominated precursor. The brominated precursor can include at least two bromo groups and at least one hydroxyl group. The reaction can cause the selected substituent to attach to the brominated precursor. In some embodiments, the compound having the selected substituent is selected from chloroacetic acid, a chloroacetate ester, a chloro-enone, 2-chloroacetamide, vinyl benzyl chloride, an acrylate benzyl chloride, a methacrylate benzyl chloride, epichlorohydrin, and allyl chloride. In other embodiments, the compound having the selected substituent is selected from glycolic acid, a glycolate ester, a hydroxy-substituted enone, N-hydroxyacetamide, a vinyl benzyl alcohol, an acryloyl benzyl alcohol, methacryloyl benzyl alcohol, glycidol, and allyl alcohol.

Further embodiments are directed to an article of manufacture that includes a polymer (e.g., a polystyrene, an epoxide resin, a polyhydroxyurethane, a polycarbonate, a polyester, a polyacrylate, a polyimide, a polyamide, a polyurea, or a poly(vinyl-ester)) and a covalently-bound polybromocyclododecane compound. The polybromocyclododecane compound can include a cyclododecane moiety with four bromo groups. In addition, the polybromocyclododecane compound can act as a crosslinker in the polymer. The article of manufacture can also include a printed circuit board and electronic components.

DETAILED DESCRIPTION

Flame-retardant compounds are commonly added to polymers in order to meet various safety regulations. For example, flame retardants can be blended into synthetic fibers that are required to comply with flame retardancy regulations (e.g., National Fire Protection Association (NFPA) 701 standards). These synthetic fibers are used in items such as electronics, clothing, acoustic dampening materials, cushioning, furniture, insulation, curtains, and carpets. Additional examples of materials that can include flame-retardant polymers include plastics, laminates, insulation, paints, coatings, foams, adhesives, and synthetic rubbers.

Additional examples of materials that can have flame-retardant additives include plastics, paints, coatings, foams, adhesives, and synthetic rubbers. These can be incorporated into devices with electronic components (e.g., printed circuit boards (PCBs), semiconductors, transistors, optoelectronics, capacitors, resistors, chip carriers, etc.). For example, resins for PCBs can be made flame retardant by incorporating polymers (e.g., epoxide resins, polyhydroxyurethane, polycarbonate, polyester, polyacrylate, polyimide, polyamide, polyurea, and/or poly(vinyl-ester) polymers) combined with flame-retardant compounds. This protects the PCBs from catching fire when exposed to high temperature environments or electrical power overloads. Further, flame retardants can be used for integrated circuit packages and other electronics hardware applications.

Common classes of flame-retardant compounds include polybrominated compounds (brominated flame retardants) and compounds having phosphate- or phosphonate-based substituents. Hexabromocyclododecane (HBCD) is a type of brominated flame retardant (BFR) that is widely used in the foam and insulation industry. For example, HBCD and its derivatives are blended into extruded and expanded polystyrene. These flame-retardant HBCD-polystyrene compositions are used in products such as upholstered furniture, automatic cushioning, interior textiles, thermal insulation, packing material, and electronics (e.g., integrated circuit packaging). However, HBCD and other BFRs can leach out of the materials in which they are embedded, and therefore have potential for bioaccumulation and toxicity. Because of these concerns, BFRs and other halogenated compounds are increasingly being targeted for elimination from consumer products.

HBCD is a polybrominated flame retardant with six bromo (—Br) groups bound to a 12-membered ring (cyclododecane):

According to some embodiments of the present disclosure, functionalized polybromocyclododecane (PBCD) flame-retardant compounds are synthesized. These functionalized PBCD flame retardants have more than two bromo groups (e.g., four or six bromo groups), and can be covalently bound to materials such as polymers and prepolymers in order to provide flame-retardant polymers. The covalent bonds between the functionalized PBCD flame retardants and the polymer chains prevent the PBCD flame retardants from leaching out of the materials into the surrounding environment. A variety of functional groups can be used in the covalent binding, which allows the production of a variety of flame-retardant materials (e.g., plastics, laminates, adhesives, fibers, rubbers, etc.) having different reactivities, structures, and properties.

Figure 1:
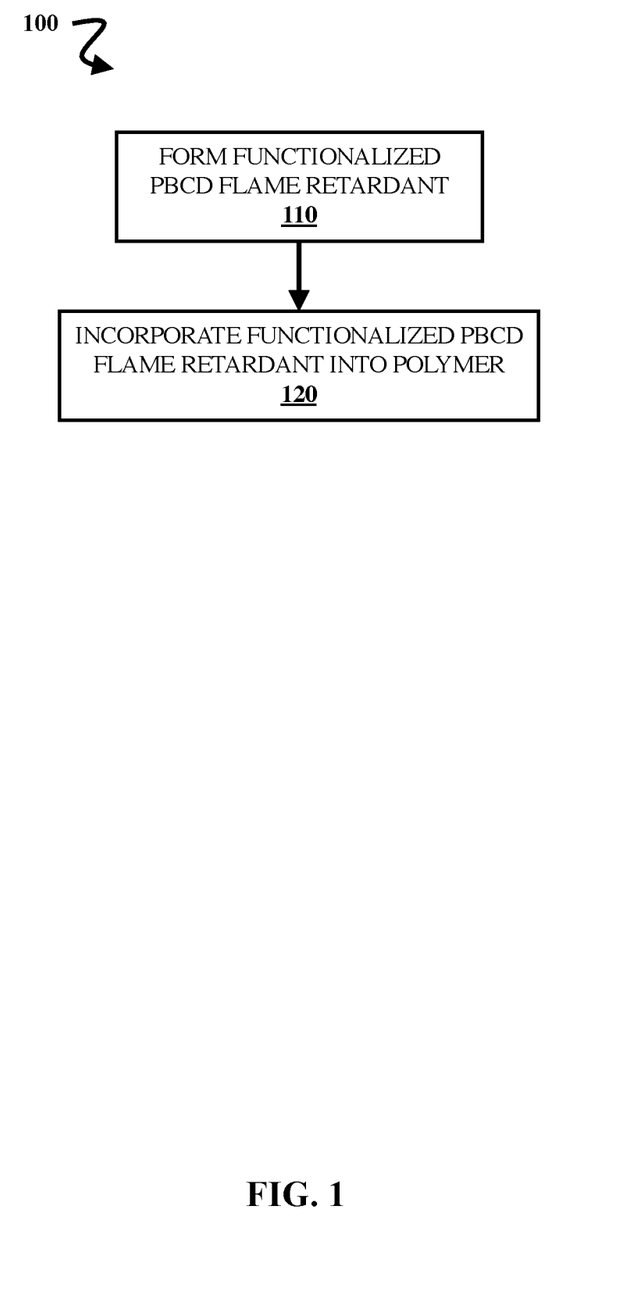
FIG. 1 is a flow diagram illustrating a process of forming a flame-retardant polymer, according to some embodiments of the present disclosure.

FIG. 1 is a flow diagram illustrating a process 100 of forming a flame-retardant polymer, according to some embodiments of the present disclosure. Process 100 begins with the provision of a functionalized polybromocyclododecane (PBCD) flame-retardant compound. This is illustrated at step 110. This step includes the preparation of compounds referred to as brominated precursors, which act as precursors to functionalized PBCD flame-retardant compounds. The brominated precursors include cyclododecane moieties having four or six bromo (—Br) groups and at least one hydroxyl (—OH) or carboxylic acid (—COOH) group. The precursors can be made using a variety of synthetic techniques, beginning with cyclododecatriene as a starting material. The structures and syntheses of various brominated precursors are discussed in greater detail with respect to FIGS. 3, 4, and 5B-6B. It also should be noted that brominated precursors may be used as functionalized PBCD flame retardants in some instances. For example, a brominated precursor having hydroxyl groups may bind to a polymer via these hydroxyl groups. A brominated precursor such as this can also be referred to as a hydroxy-PBCD flame retardant. This is discussed in greater detail below.

Other reactive functional groups can also be added to the brominated precursors in order to form functionalized PBCD flame retardants. Herein, "reactive functional group" refers to a moiety that can form a covalent bond to another compound, such as a small molecule (e.g., molecules having a molecular weight below approximately 900 daltons), oligomer, or polymer. These reactive functional groups are also referred to herein as "functional groups" for simplicity. Unless otherwise specified, a functional group is a reactive functional group. A functionalized PBCD flame retardant is a PBCD flame-retardant compound that is able to covalently bind to other compounds by its reactive functional group(s). These functional groups can be part of a larger substituent that is bound to the PBCD flame retardant. For example, a substituent may include a $C_1$ to $C_{20}$ linear or branched alkyl moiety having at least one terminal vinyl or epoxide functional group. Substituents and terminal functional groups are discussed in greater detail with respect to FIG. 2.

The identity of the functional group added to the brominated precursor is controlled by the selection of compounds reacted with the precursor. For example, a brominated precursor having a hydroxyl group can be reacted with an organohalide having a selected reactive functional group. This reaction results in the selected functional group replacing the hydroxyl group. Additionally, functional groups can be added to brominated precursors having carboxylic acid groups by reactions with hydroxy-functionalized compounds (e.g., alcohols) that include the selected reactive functional group. These reactions bind the selected functional group at the location of the carboxylic acid group. Examples of organohalides and hydroxy-functionalized compounds that can be used are discussed in greater detail with respect to FIGS. 3 and 5D, respectively.

The identity of the functional groups can also be varied by carrying out additional reactions to modify the functionalized PBCD flame retardants. For example, PBCD flame retardants with vinyl (—CH=CH$_2$) functional groups can be reacted with thiol compounds having additional functional groups, such as carboxylic acid (—COOH), hydroxyl (—OH), or amine (—NH$_2$) groups, in order to form functionalized thioether substituents. Additionally, epoxide-functionalized PBCD flame retardants can be reacted with lithium bromide (LiBr) and carbon dioxide (CO$_2$) in order to produce a propylene carbonate functional group. Reactions to provide these modifications are discussed in greater detail with respect to FIG. 7.

The functionalized PBCD flame retardants are then incorporated into polymers in order to produce flame-retardant materials. This is illustrated at step 120. The functionalized PBCD flame retardants form covalent bonds to the polymer chains. In some embodiments, the bound PBCD flame retardants act as crosslinkers. However, it is also possible for the functionalized PBCD flame retardants to bind to only one location on a polymer chain. Examples of polymers that can be made flame-retardant by incorporation of the functionalized PBCD flame retardants include polystyrenes, epoxide resins, polyhydroxyurethanes, polycarbonates, polyesters, polyacrylates, polyimides, polyamides, polyureas, poly(vinyl-esters), and mixtures, co-polymers, or prepolymers thereof.

In some embodiments, the functionalized PBCD flame retardants bind to polymer chains when blended during processing of the polymer. However, the functionalized PBCD flame retardants can also covalently bind to prepolymers (e.g., monomers or systems of monomers). When these prepolymers are polymerized, the resulting flame-retardant polymer includes the covalently-bound PBCD flame retardants. In other embodiments, flame-retardant polymers can be formed using a functionalized PBCD flame retardant as a class of monomer. This results in a polymer or co-polymer that includes PBCD flame-retardant repeat units.

Other materials may be added to the flame-retardant polymers. For example, additional crosslinkers can be added. Examples of crosslinking chemistries can include sulfur vulcanization and reactions with peroxides, such as tert-butyl perbenzoate, dicumyl peroxide, benzoyl peroxide, and di-tert-butyl peroxide. Other materials that may be blended with the compounds and polymers described herein can include additives such as anti-oxidants, glass fillers, carbon fillers, anti-drip agents, anti-static agents, branching resins, impact-modifiers, plasticizers, lubricants, mold release agents, and/or molecular weight regulators.

Materials that include the resulting flame-retardant polymers can include plastics, laminates, synthetic fibers, insulation, paints, coatings, foams, adhesives, and synthetic rubbers. These can be incorporated into devices with electronic components (e.g., printed circuit boards (PCBs), semiconductors, transistors, optoelectronics, capacitors, resistors, chip carriers, etc.). Further, the flame-retardant materials can be used for integrated circuit packages and other electronics hardware applications, as well as articles such as upholstered furniture, automotive cushioning, interior textiles, thermal insulation, packing material, etc.

Figure 2:
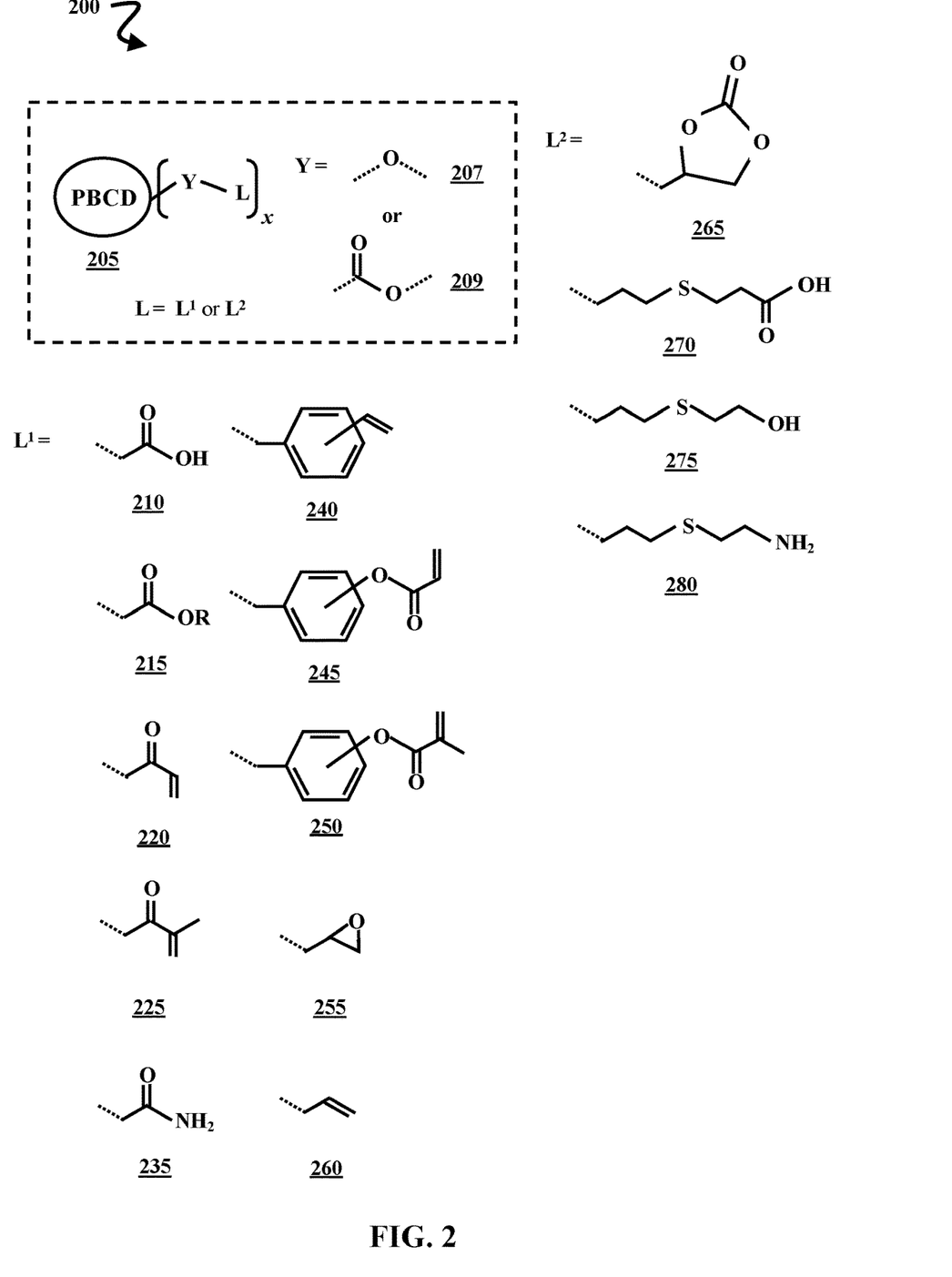
FIG. 2 is a chemical structure diagram illustrating structural components of functionalized polybromocyclododecane (PBCD) flame retardants, according to some embodiments of the present disclosure.

FIG. 2 is a chemical structure diagram illustrating structural components 200 of functionalized PBCD flame retardants, according to some embodiments of the present disclosure. A generic functionalized PBCD flame retardant 205 is illustrated as having substituents that include an L group attached by a Y linker to an oval labeled "PBCD". In some embodiments, the number of substituents (x) is one or two. However, more substituents may be attached in other embodiments (e.g., three or four substituents). The oval represents the polybromocyclododecane moiety and any other moieties present in a functionalized PBCD flame retardant 205 (e.g., substituted or unsubstituted methylene spacer (—CH$_2$—) groups between Y and the cyclododecane ring). The Y linker is either an oxygen atom 207 or an ester 209, depending upon the starting materials and reaction conditions.

The L functional group is either $L^1$ or $L^2$. The substituents represented by $L^1$ are those that are added directly to the PBCD moiety by a reaction involving a compound of the formula HO-$L^1$ or X-$L^1$ (where X=Cl or Br). Additional reactions are carried out with $L^1$-PBCD compounds to form $L^2$ substituents in some embodiments. For simplicity, the L groups are referred to herein using names based on their functionality alone, rather than a functional group they may become part of after binding to the oxygen atom 207 or ester 209 of the PBCD compound 205. For example, $L^1$ group 210 is referred to as a carboxylic acid group. However, when the carboxylic acid group 210 is in a PBCD compound 205 where Y is an oxygen atom 207, the $L^1$ group 210 becomes part of a carbonate functional group. When Y is an ester linker 209, the carboxylic acid group 210 becomes part of an oxalate group.

Likewise, $L^1$ group 215 is referred to as an ester 215, though it too can either be part of a carbonate or an oxalate functional group in the PBCD compound 205, depending upon the identity of Y. The ester 215 includes an R group. Herein, "R group" refers to a hydrocarbyl moiety with or without heteroatoms (e.g., nitrogen, oxygen, halogens, sulfur, etc.) unless otherwise specified. Examples of hydrocarbyl substituents that can be included in the ester 215 L group include cyclic and/or acyclic aliphatic moieties optionally containing one or more double and/or triple bonds (e.g., alkyl, alkenyl, alkynyl, cycloalkyl, cycloalkenyl, alkaryl, and aralkyl groups). The acyclic aliphatic groups can be branched or unbranched. In some embodiments, the R groups have reactive moieties such as vinyl, epoxide, allyl, amine, carboxylate, propylene carbonate, and hydroxyl.

Additional examples of $L^1$ groups illustrated in FIG. 2 include an acryloyl 220, a methacryloyl 225, and a primary amide 235. The $L^1$ groups can also be substituted benzyl groups. The substituents can be bound at meta, para, or ortho positions relative to the PBCD moiety. Examples of substituted benzyl $L^1$ groups include an allyl-substituted benzyl 240, an acryloyl-substituted benzyl 245, and a methacryloyl-substituted benzyl 250. Further, the $L^1$ groups can be epoxide 255 or allyl 260 groups. Compounds 205 having epoxide $L^1$ groups 255 can be reacted to form propylene carbonate $L^2$ groups 265, and compounds 205 having allyl $L^1$ groups 260 can be reacted to form thioether $L^2$ groups 270, 275, and 280. This is discussed in greater detail with respect to FIG. 7.

The list of L functional groups illustrated in FIG. 2 should not be interpreted as limiting. Other reactive moieties can be in the place of L groups on the covalently-bound flame retardants disclosed herein. For example, the syntheses of hydroxy- and carboxylic acid-functionalized PBCD flame retardants are illustrated in FIGS. 3, 4, and 5B-6B. Further, any appropriate reactive functional groups known to a person of ordinary skill in the art can be added, depending upon the availability of starting materials and other reaction components.

Figure 3:
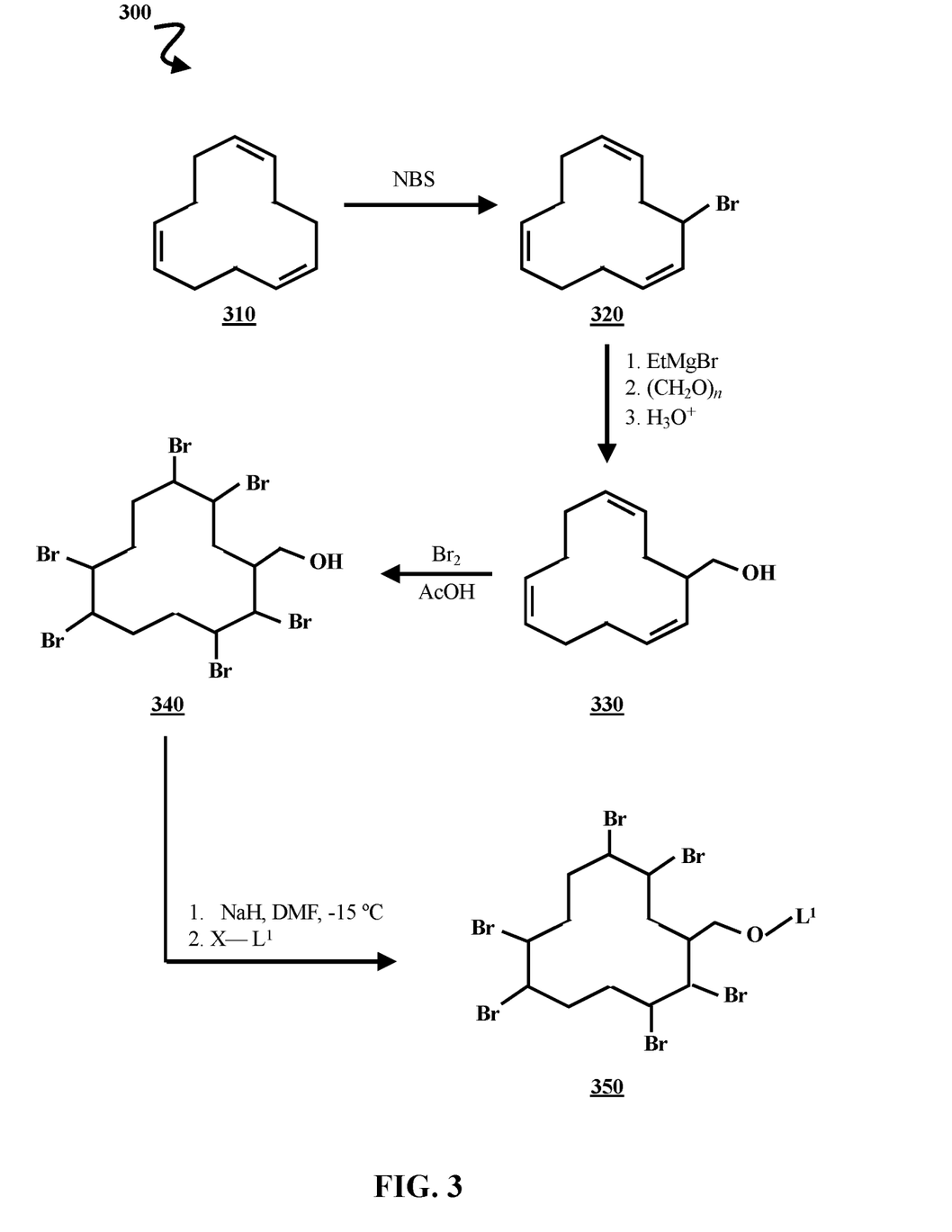
FIG. 3 is a chemical reaction diagram illustrating a first process of forming a mono-$L^1$-PBCD flame-retardant compound from 1,5,9-cyclododecatriene (CDT), according to some embodiments of the present disclosure.

FIG. 3 is a chemical reaction diagram illustrating a first process 300 of forming a mono-$L^1$-PBCD flame-retardant compound from 1,5,9-cyclododecatriene (CDT) 310, according to some embodiments of the present disclosure. Process 300 includes radical bromination of CDT 310. The radical bromination is carried out by reacting CDT 310 with one equivalent of N-bromosuccinimide (NBS) and a radical initiator, such as an azo compound (e.g., 2,2-azobisisobutyronitrile or azobenzene), an organic peroxide (e.g., dibenzoyl peroxide, di-tert-butyl peroxide, cyclohexenyl hydroperoxide, methyl ethyl ketone peroxide, etc.), an inorganic peroxide (e.g., peroxydisulfate), or ultraviolet (UV)

light. The bromination is carried out in carbon tetrachloride, dichloromethane, acetonitrile, or a mixture thereof, and refluxed for approximately 1-5 hours (h). The mixture is then cooled and filtered to remove succinimide. The succinimide is washed, and the washings are added to the filtrate. The filtrate is then dried using magnesium sulfate ($MgSO_4$), followed by concentration under reduced pressure. Fractional distillation of the filtrate yields 3-bromocyclododeca-1,5,9-triene 320.

The 3-bromocyclododeca-1,5,9-triene 320 is then converted into a Grignard reagent (not shown) in a reaction with ethylmagnesium bromide (EtMgBr), though isopropylmagnesium bromide may be used instead of EtMgBr in some embodiments. In other embodiments, the Grignard may be prepared by reacting 3-bromocyclododeca-1,5,9-triene 320 with magnesium metal. The reaction to prepare a Grignard reagent is carried out under a substantially inert atmosphere (e.g., nitrogen and/or argon) in an aprotic solvent (e.g., diethyl ether and/or tetrahydrofuran). In a second step, the Grignard reagent is reacted with paraformaldehyde ($CH_2O)_n$, followed by hydrolysis under acidic conditions ($H_3O^+$), to produce a hydroxylated CDT compound referred to herein as CDT methanol 330. The CDT methanol 330 is then brominated by treatment with bromine ($Br_2$) in glacial acetic acid (AcOH). The solution of CDT methanol 330 and $Br_2$ in AcOH is cooled with an ice bath, and reacted for about 0.5 h before being warmed to room temperature. The reaction is allowed to proceed for approximately 12 h at room temperature, yielding hexabromocyclododecane (HBCD) methanol 340.

The HBCD methanol 340 can be used as a covalently-bound PBCD flame retardant through its hydroxyl functional group. However, the hydroxyl group on the HBCD methanol 340 can also be used as a site of attachment for another desired L functional group. In these instances, the HBCD methanol 340 acts a brominated precursor. The reaction to attach an $L^1$ functional group is carried out in the presence of sodium hydride (NaH) at a low temperature (e.g., about −15° C.) in a dimethylformamide (DMF) solution. These reaction conditions promote substitution chemistry over elimination of the bromo groups on the cyclododecane ring.

An organohalide of the desired $L^1$ group (X-$L^1$, where X is chloro (Cl) or bromo (Br)) is added to the reaction mixture. Examples of organohalides that can be used include chloroacetic acid to give $L^1$ group 210; a chloroacetate ester such as methyl chloroacetate, ethyl chloroacetate, benzyl chloroacetate to give $L^1$ group 215; chloro-enones to give $L^1$ groups 220 and 225; 2-chloroacetamide to give $L^1$ group 235; 2-, 3-, or 4-vinyl benzyl chloride to give $L^1$ group 240; 2-, 3-, or 4-methacrylate benzyl chloride to give $L^1$ group 245; 2-, 3-, or 4-acrylate benzyl chloride to give $L^1$ group 245; epichlorohydrin to give $L^1$ group 255; and allyl chloride to give $L^1$ group 260 (shown in FIG. 2). The resulting substitution reaction produces a mono-$L^1$-PBCD flame retardant 350 where the Y linker is an oxygen atom 207 with a methylene spacer group between it and the cyclododecane ring.

Figure 4:
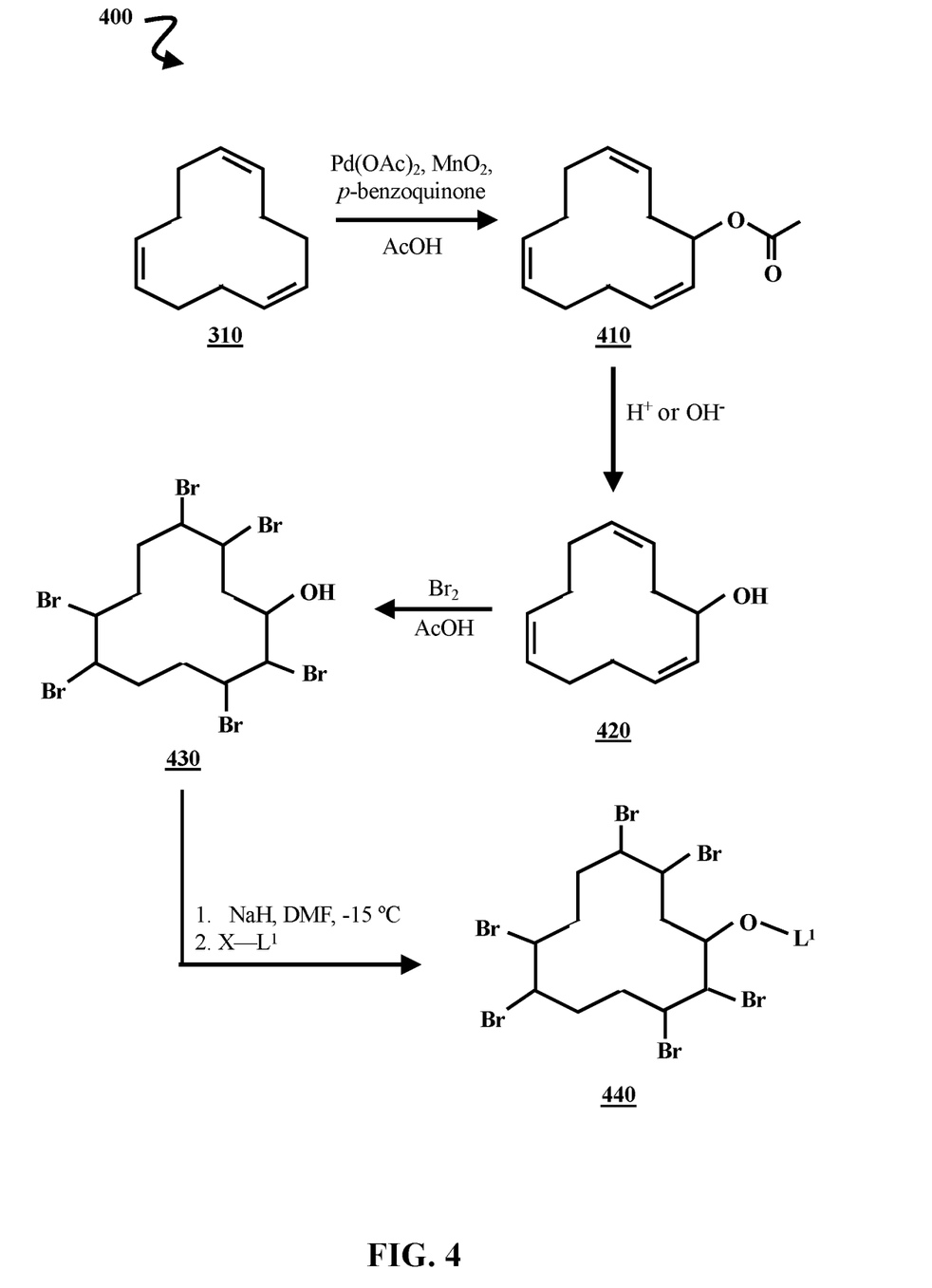
FIG. 4 is a chemical reaction diagram illustrating a second process of forming a mono-$L^1$-PBCD flame-retardant compound from CDT, according to some embodiments of the present disclosure.

FIG. 4 is a chemical reaction diagram illustrating a second process 400 of forming a mono-$L^1$-PBCD flame-retardant compound from 1,5,9-cyclododecatriene (CDT) 310, according to some embodiments of the present disclosure. Process 400 includes acetylation of CDT 310. The acetylation reaction uses approximately 5-10 mol % palladium(II) acetate (Pd(OAc)$_2$) in the presence of approximately 1.5-2 equivalents each of p-benzoquinone and optionally another oxidative additive. In process 400, p-benzoquinone and manganese(IV) oxide ($MnO_2$) are the oxidative additives. Other oxidants that may be added can include dimethylsulfoxide (DMSO) or its derivatives, substituted benzoquinones, and metal salts such as copper(II) chloride, copper(II) acetate, and silver(I) oxide. The reaction is carried out using acetic acid (AcOH) as a solvent. In some embodiments, the reaction is maintained at temperatures around 60° C. for approximately 10-20 h. However, the reaction time and temperature can be adjusted (e.g., 2 h at 80° C. or 24 h at 20° C.-30° C.), as is understood by a person of ordinary skill in the art.

An aqueous solution of the acetylated CDT 410 resulting from this reaction is prepared, and its acyl group is removed in a hydrolysis reaction, resulting in a hydroxy-CDT 420. This hydrolysis reaction can be carried out in the presence of either an acid ($H^+$) or a base ($OH^-$). The hydroxy-CDT 420 is then brominated by treatment with Br$_2$ in AcOH. This produces a compound referred to herein as hydroxy-hexabromocyclododecane (hydroxy-HBCD) 430, which can be used as a covalently-bound PBCD flame retardant through its hydroxyl functional group (—OH). However, the hydroxyl group on the hydroxy-HBCD 430 can also be used as a site of attachment for a selected $L^1$ functional group. As in process 300, the reaction to attach an $L^1$ functional group is carried out in the presence of sodium hydride at a low temperature (e.g., about −15° C.). An organohalide of the $L^1$ group (X-$L^1$) is added to the reaction mixture. The resulting substitution reaction produces a mono-$L^1$-PBCD flame retardant 440 where the Y linker is an oxygen atom 207 bonded directly to the cyclododecane ring.

Figure 5A:
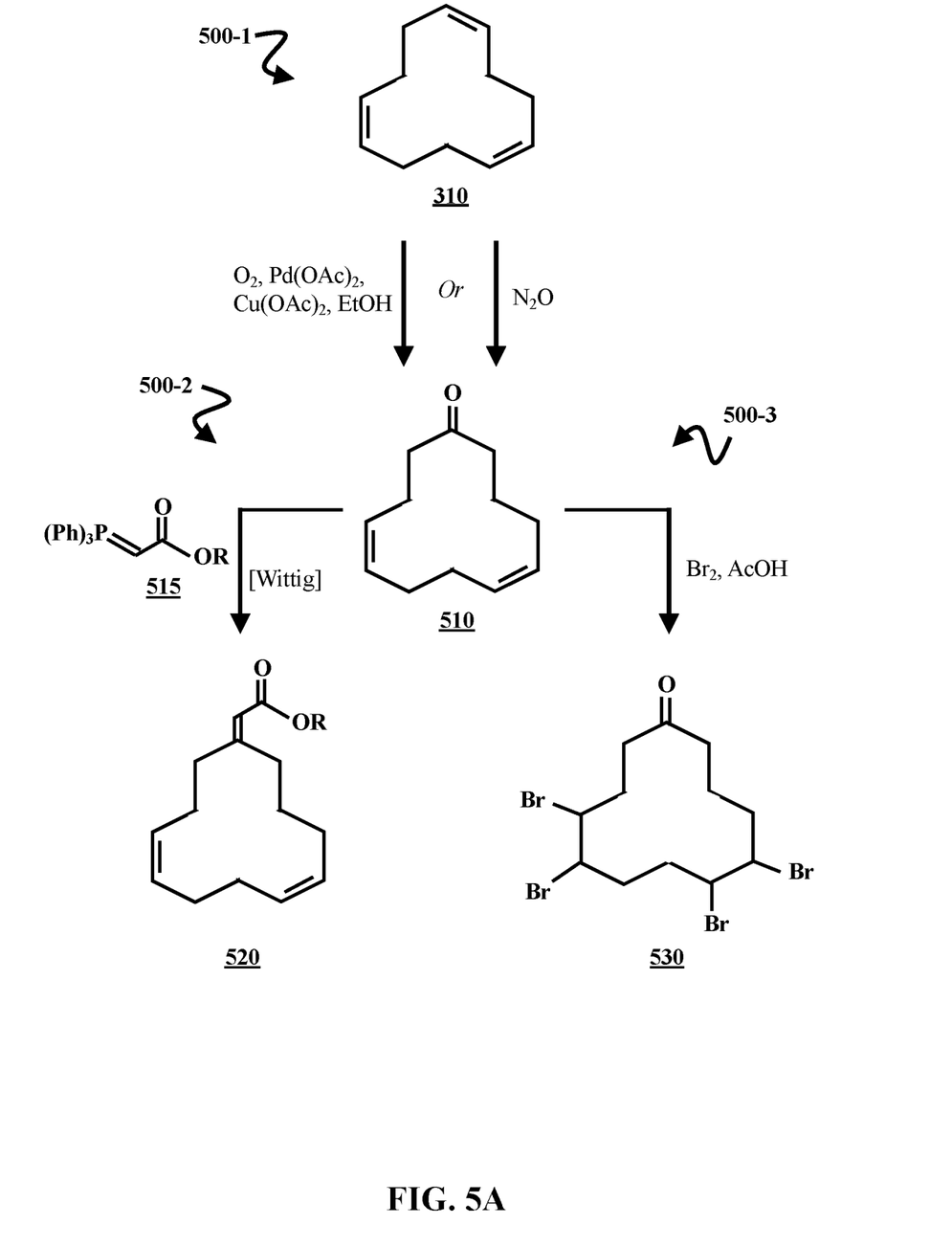
FIG. 5A is a chemical reaction diagram illustrating processes of preparing precursor compounds for functionalized PBCD flame retardants, according to some embodiments of the present disclosure.

FIG. 5A is a chemical reaction diagram illustrating processes 500-1, 500-2, and 500-3 of preparing precursor compounds for functionalized PBCD flame retardants, according to some embodiments of the present disclosure. Process 500-1 includes the oxidation of CDT 310 to form a ketone-substituted cyclododecadiene (CDD ketone) 510. Two alternative methods for carrying out this oxidation are illustrated. The first of these is an aerobic palladium(II)-catalyzed oxidation, which uses Pd(OAc)$_2$ in the presence of copper(II) acetate (Cu(OAc)$_2$) to catalyze a reaction between molecular oxygen (O$_2$) and CDT 310. In some embodiments, the reaction is carried out in ethanol at an air pressure of about 25 bar and a temperature of about 100° C., though other solvents (e.g., methanol), pressures (e.g., about 20 bar-60 bar), and temperatures (e.g., about 50° C.-110° C.) can be used.

The second example method for forming the CDD ketone 510 in process 500-1 involves a reaction between CDT 310 and nitrous oxide (N$_2$O). CDT 310 is introduced into an autoclave, which is then sealed and purged with nitrogen (N$_{2(g)}$). The autoclave is then pressurized with N$_2$O up to about 30 atm. The temperature is increased to about 225° C., and the maximum pressure during the reaction is about 54 atm while heating. The reaction is allowed to proceed for about 50 h, at which point the autoclave is cooled and decompressed. The product of the reaction, which can optionally be analyzed by quantitative gas chromatography (GC) and/or GC-mass spectrometry (GC-MS), is the CDD ketone 510.

The CDD ketone 510 is reacted further in process 500-2 or 500-3. In process 500-2, the CDD ketone 510 is reacted with a phosphonium ylide 515 under Wittig reaction conditions. The phosphonium ylide 515 is formed in situ using synthetic steps commonly known in the art. However, the phosphonium ylide 515 can also be obtained from commercial sources in some embodiments. This step results in attachment of an ester group 215 to the cyclododecadiene ring by a carbon-carbon double bond. The product of this reaction is referred to herein as CDD ester 520. Examples of R groups that can be on the ester moiety provided by the ylide 515 are discussed in greater detail with respect to FIG. 2. It should be noted that, in some embodiments, the phosphonium ylide 515 having an ester moiety can be replaced by an ylide having a carboxylic acid moiety instead, resulting in an analogous CDD carboxylic acid (see FIG. 5D).

In process 500-3, the CDD ketone 510 is brominated in a reaction with $Br_2$ in AcOH. This bromination reaction is carried out under substantially similar conditions to the bromination of CDT methanol 330 to form HBCD methanol 340. Bromination reaction conditions are discussed in greater detail with respect to FIG. 3. Bromination of the CDD ketone 510 provides a product referred to herein as tetrabromocyclododecane (TBCD) ketone 530. This compound 530 can act as a flame retardant, and it can be reacted in subsequent steps to attach L functional groups.

Figure 5B:
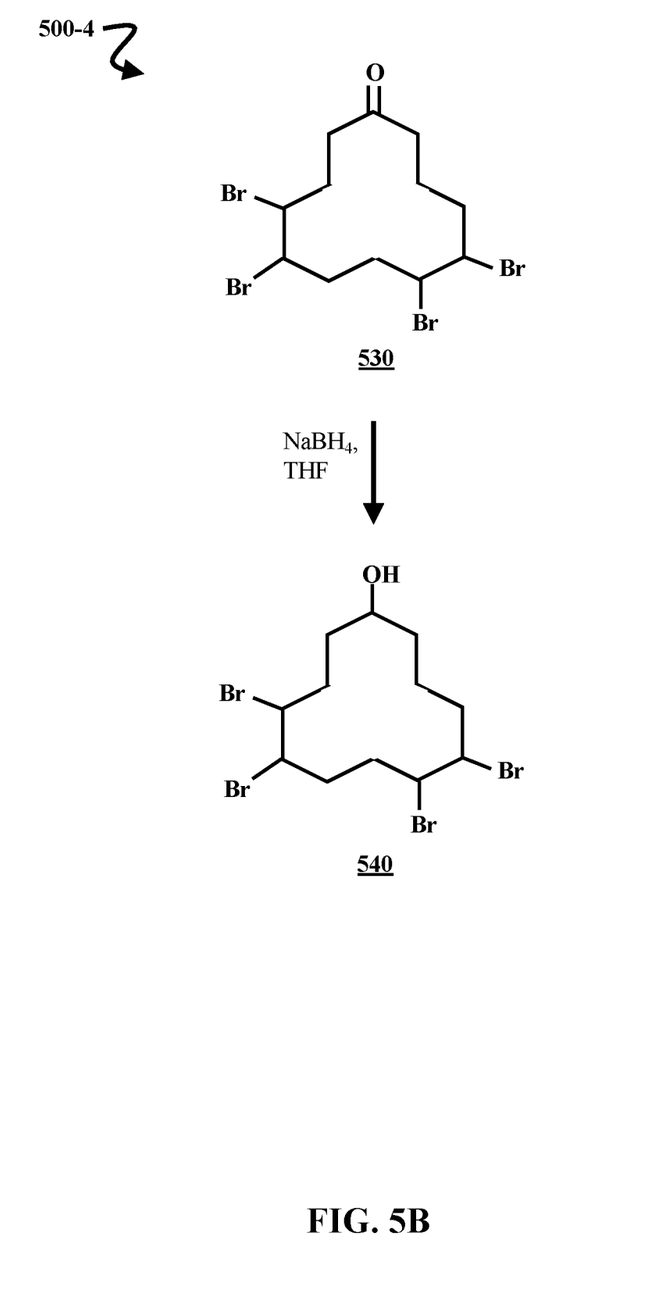
FIG. 5B is a chemical reaction diagram illustrating a process of forming a hydroxy-PBCD flame retardant from a tetrabromocyclododecane (TBCD) ketone, according to some embodiments of the present disclosure.

FIG. 5B is a chemical reaction diagram illustrating a process 500-4 of forming a hydroxy-PBCD flame retardant from the TBCD ketone 530, according to some embodiments of the present disclosure. In process 500-4, the TBCD ketone 530 is combined with sodium borohydride ($NaBH_4$) in a tetrahydrofuran (THF) solution. The $NaBH_4$ reduces the ketone moiety to form a hydroxyl group. The resulting polybrominated compound referred to herein as hydroxy-PBCD flame retardant 540. Hydroxy-PBCD 540 can be used as a covalently-bound flame retardant through its hydroxyl functional group. However, hydroxy-PBCD 540 can also be used as a brominated precursor.

Figure 5C:
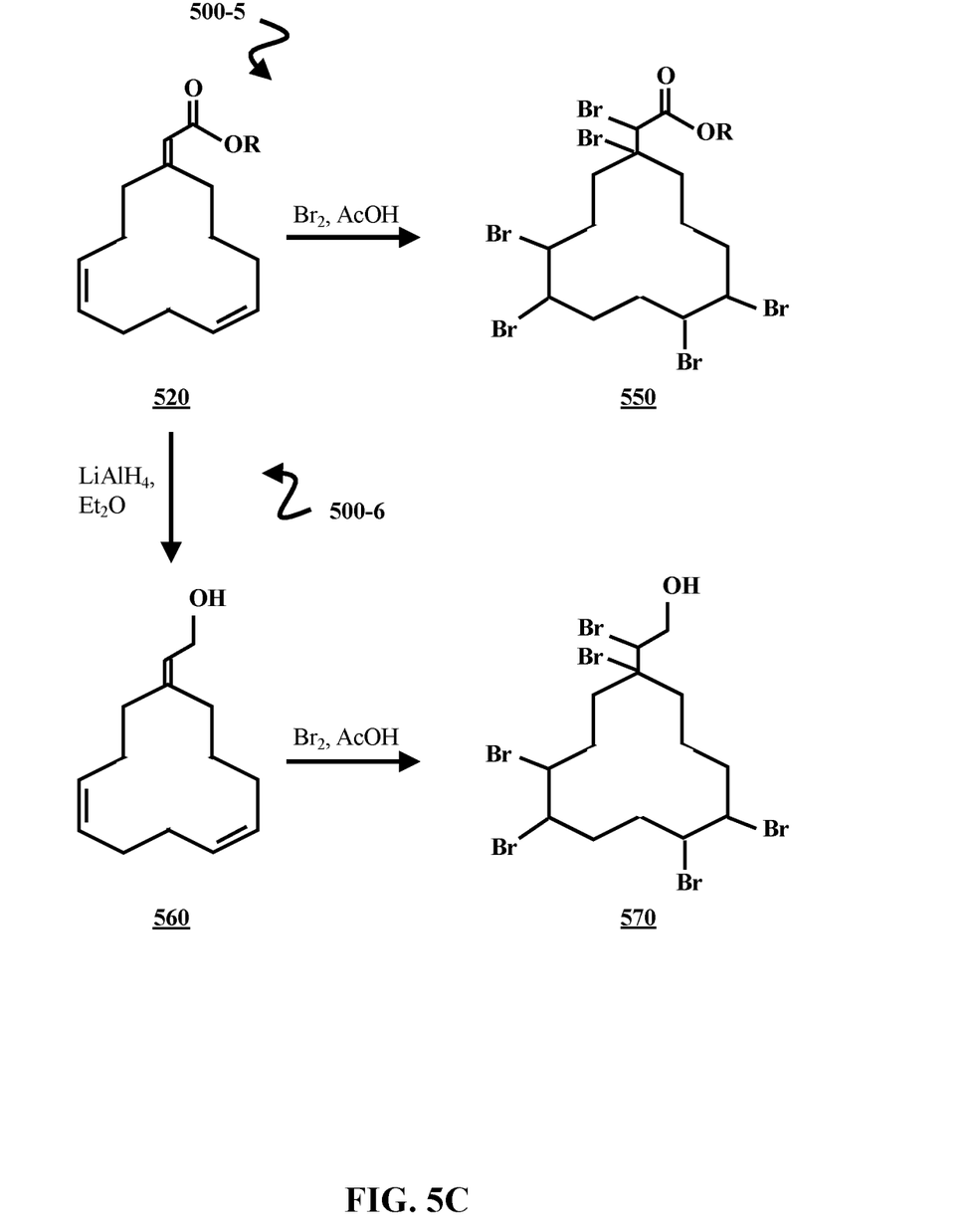
FIG. 5C is a chemical reaction diagram illustrating processes of forming hydroxy-PBCD flame retardants from a cyclododecadiene (CDD) ester, according to some embodiments of the present disclosure.

FIG. 5C is a chemical reaction diagram illustrating processes 500-5 and 500-6 of forming hydroxy-functionalized PBCD flame retardants from the CDD ester 520, according to some embodiments of the present disclosure. In process 500-5, the CDD ester 520 is brominated by treatment with $Br_2$ in AcOH under reaction conditions substantially similar to those of the bromination reactions illustrated in FIG. 3. The bromination 500-5 produces a PBCD flame retardant with five bromo groups on its cyclododecane ring and one bromo group on a carbon between the ester Y linker 209 and the ring. This PBCD flame retardant is referred to herein as ester-PBCD flame retardant 550. However, if a phosphonium ylide having a carboxylic acid moiety (—COOH) replaces the ylide 515 having an ester moiety (—COOR) in process 500-2, the ester-PBCD flame retardant 550 will instead be an analogous carboxylic acid-PBCD flame retardant. This carboxylic acid-PBCD flame retardant is illustrated in FIG. 5D.

In process 500-6, the CDD ester 520 is combined with lithium aluminum hydride ($LiAlH_4$) in diethyl ether ($Et_2O$). The $LiAlH_4$ reduces the ester moiety of the CDD ester 520. This results in a CDD allyl alcohol 560, upon quenching the reaction with 1N HCl (aq) solution. The allyl alcohol moiety is bound to the cyclododecadiene ring by a carbon-carbon double bond. The CDD allyl alcohol 560 is brominated using techniques substantially similar to those for producing HBCD methanol 340 (e.g., treatment with $Br_2$ in AcOH). Bromination takes place at each carbon-carbon double bond of the starting compound 560, resulting in a brominated cyclododecane ring having a brominated ethanol substituent (—$CHBrCH_2OH$). This compound is referred to herein as an ethanol-PBCD flame retardant 570. The ethanol-PBCD flame retardant 570 includes a total of six bromo groups, where five of the bromo groups are on the cyclododecane moiety, and one is on a carbon between the hydroxyl group and the ring. The ethanol-PBCD flame retardant 570 can bind to polymers through its hydroxyl group, or it can be reacted further as a brominated precursor.

Figure 5D:
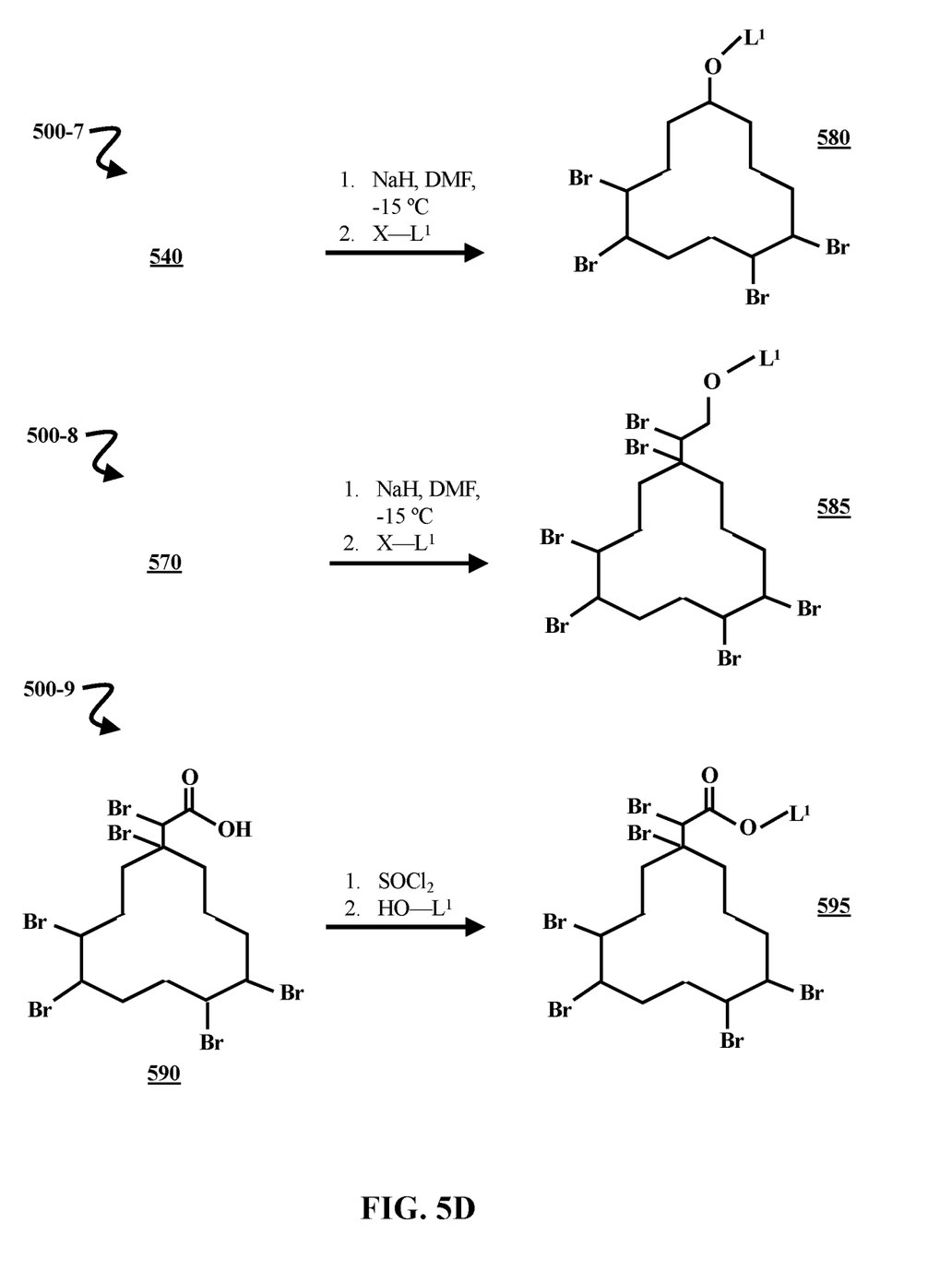
FIG. 5D is a chemical reaction diagram illustrating processes of forming $L^1$-functionalized PBCD flame retardants from brominated precursors, according to some embodiments of the present disclosure.

FIG. 5D is a chemical reaction diagram illustrating processes 500-7, 500-8, and 500-9 of forming $L^1$-functionalized PBCD flame retardants from brominated precursors, according to some embodiments of the present disclosure. The brominated precursors are also referred to as hydroxy- or carboxylic acid-PBCD flame retardants herein. This is discussed in greater detail above. Processes 500-7 and 500-8 are two examples of reactions between $X-L^1$ compounds and hydroxy-PBCD flame retardants, and process 500-9 is an example of a reaction between an $HO-L^1$ compound and a carboxylic acid-PBCD flame retardant.

In processes 500-7 and 500-8, the $X-L^1$ compounds are reacted with hydroxy-functionalized PBCD flame retardants 540 and 570 in the presence of sodium hydride (NaH) at low temperatures (e.g., about −15° C.) in order to attach the selected $L^1$ group at an oxygen atom Y linker 207. Examples involving substantially similar reaction conditions are discussed in greater detail with respect to FIGS. 3 and 4. Examples of organohalides ($X-L^1$) that can be used are also discussed in greater detail with respect to FIG. 3. In process 500-7, hydroxy-PBCD flame retardant 540, which was formed in process 500-4 (FIG. 5B), is reacted with $X-L^1$. This results in a polybrominated flame retardant referred to herein as $L^1$-PBCD flame retardant 580. In process 500-8, ethanol-PBCD flame retardant 570 (process 500-6, FIG. 5C) is reacted with $X-L^1$, resulting in a polybrominated flame retardant referred to herein as $L^1$-PBCD flame retardant 585.

Process 500-9 is a reaction to attach an $L^1$ functional group to a carboxylic acid-functionalized PBCD flame retardant 590. The synthesis of PBCD flame retardant 590 is not illustrated in FIG. 5C. However, the synthesis is accomplished in a Wittig reaction with a carboxylic acid-phosphonium ylide and CDD ketone 510 under substantially similar conditions to the Wittig reaction of process 500-2 (FIG. 5A). The resulting PBCD flame retardant 590 is combined with thionyl chloride ($SOCl_2$), which converts the carboxylic acid functionality into an acid chloride. This acid chloride-functionalized intermediate (not shown) is then combined with a hydroxy-functionalized compound that includes an $L^1$ group ($HO-L^1$). The resulting reaction produces a PBCD flame retardant having the selected $L^1$ group and an ester Y linker 209. This flame retardant is referred to herein as $L^1$-PBCD flame retardant 595.

The $HO-L^1$ compounds used to react with carboxylic acid-PBCD flame retardants (e.g., PBCD flame retardant 590) are analogous to the $X-L^1$ compounds that react with hydroxy-PBCD flame retardants. Examples of $HO-L^1$ compounds that can be used include glycolic acid to give $L^1$ group 210; a glycolate ester to give $L^1$ group 215; hydroxy-substituted enones to give $L^1$ groups 220 and 225; N-hydroxyacetamide to give $L^1$ group 235; 2-, 3-, or 4-vinyl benzyl alcohol to give $L^1$ group 240; 2-, 3-, or 4-acryloyl benzyl alcohol to give $L^1$ group 245; 2-, 3-, or 4-methacryloyl benzyl alcohol to give $L^1$ group 245; glycidol to give $L^1$ group 255; and allyl alcohol to give $L^1$ group 260 (shown in FIG. 2).

Figure 6A:
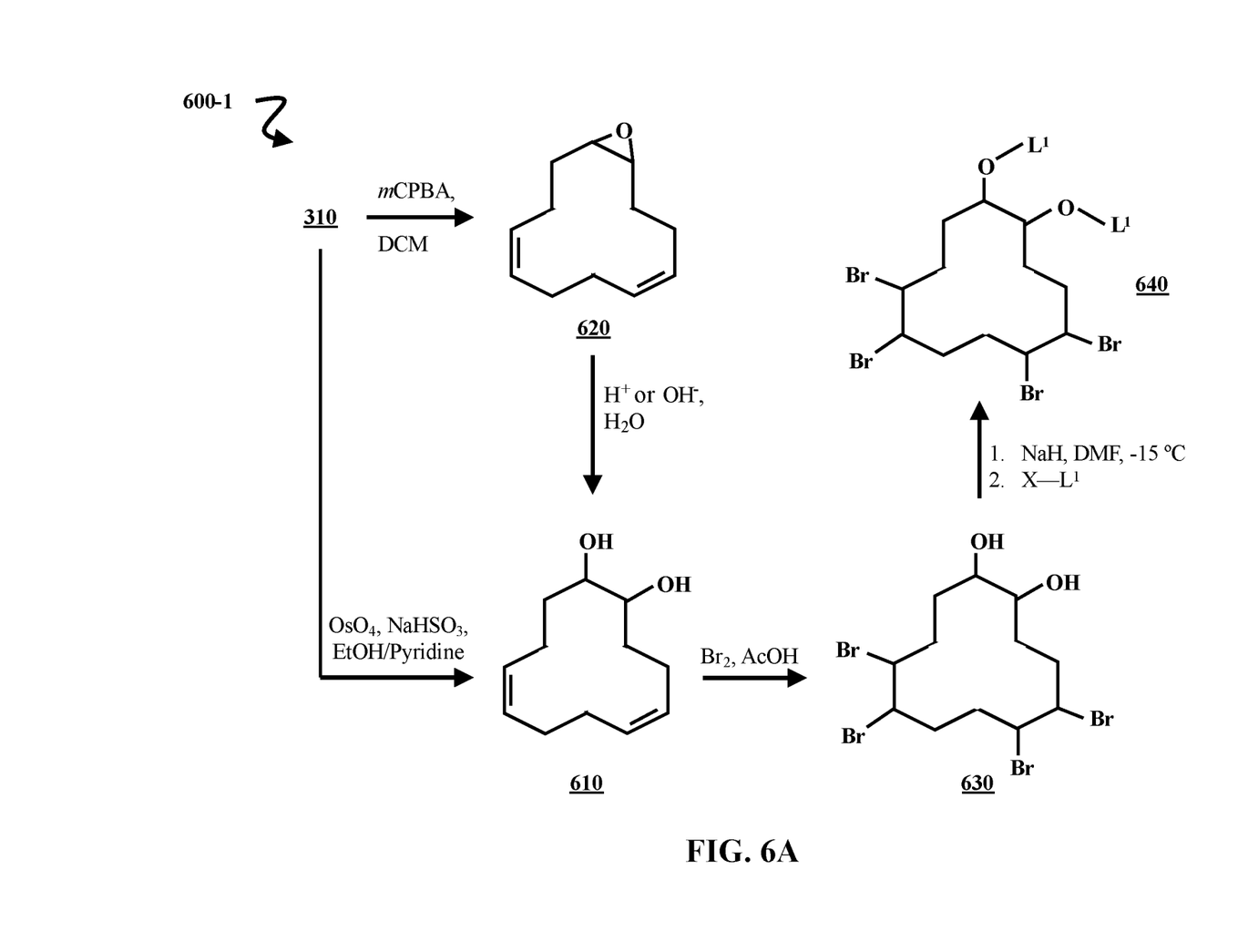
FIG. 6A is a chemical reaction diagram illustrating a process of forming difunctionalized polybromocyclododecane (di-$L^1$-PBCD) flame retardants, according to some embodiments of the present disclosure.

FIG. 6A is a chemical reaction diagram illustrating a process 600-1 of forming difunctionalized PBCD (di-$L^1$-PBCD) flame retardants, according to some embodiments of the present disclosure. The reaction involves a diol-cyclododecadiene (CDD) intermediate 610. Two methods of forming this intermediate 610 are illustrated in FIG. 6A. In one of the methods, CDT 310 is reacted with an oxidant, m-chloroperoxybenzoic acid (mCPBA), in a dichloromethane (DCM) solution. This reaction forms an epoxide-CDD intermediate 620. Hydrolysis of the epoxide group on the intermediate 620 under either acidic (H+) or basic (OH−) conditions results in the diol-CDD intermediate 610.

The diol-CDD intermediate 610 can also be formed in a method that involves reacting CDT 310 with osmium tetroxide ($OsO_4$) in a mixture of ethanol (EtOH) and pyridine. This step is carried out at approximately 0° C. for about 2 h. The oxidation reaction with $OsO_4$ produces an osmate ester intermediate (not shown). The osmate ester moiety in this intermediate is reduced in a reaction with sodium bisulfite ($NaHSO_3$). However, potassium bisulfite ($KHSO_3$) can be used as a reducing agent in some embodiments. The reduction reaction is allowed to proceed at room temperature for approximately 12 h, yielding the diol-CDD intermediate 610.

The diol-CDD intermediate 610 is brominated by treatment with $Br_2$ in AcOH to form a PBCD flame-retardant compound having two hydroxyl groups, referred to herein as diol-PBCD flame retardant 630. Example $Br_2$/AcOH bromination reaction conditions are discussed in greater detail with respect to FIG. 3. Diol-PBCD flame retardant 630 can bind to a polymer or prepolymer through its hydroxyl groups. However, diol-PBCD flame retardant 630 can also act as a brominated precursor to other PBCD flame retardants. In these instances, diol-PBCD flame retardant 630 is combined with NaH in DMF at approximately −15° C. An organohalide with a selected $L^1$ group ($X-L^1$) is added to the reaction, resulting in a di-$L^1$-substituted PBCD flame-retardant compound referred to herein as di-$L^1$-PBCD flame retardant 640. Reaction conditions and choices of $X-L^1$ compound for this type of reaction are discussed in greater detail above.

Figure 6B:
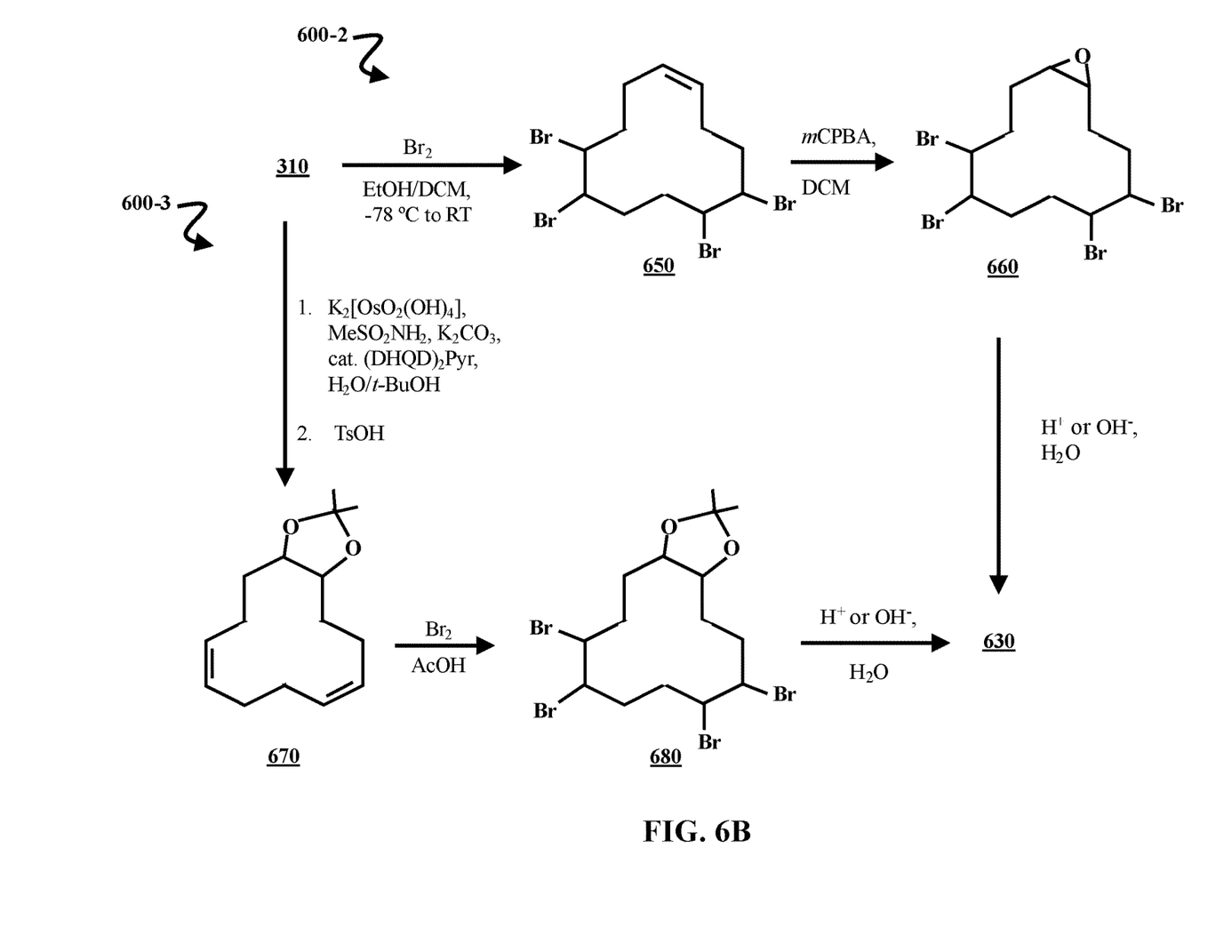
FIG. 6B is a chemical reaction diagram illustrating processes of forming a diol-PBCD flame retardant, according to some embodiments of the present disclosure.

FIG. 6B is a chemical reaction diagram illustrating additional processes 600-2 and 600-3 of forming diol-PBCD flame retardant 630, according to some embodiments of the present disclosure. In process 600-2, CDT 310 is partially brominated to form a tetrabromocyclododecene 650. This is accomplished by adding $Br_2$ to an EtOH/DCM solution of CDT 310. The reaction is carried out at approximately −78° C. for about 1 h (e.g., using a dry ice ($CO_{2(s)}$)/acetone bath), at which point the mixture is warmed to room temperature. The reaction is allowed to proceed at room temperature for about 2 h, resulting in the formation of tetrabromocyclododecene 650. Tetrabromocyclododecene 650 is then reacted with mCPBA in DCM to produce an epoxide intermediate 660. The epoxide intermediate 660 is hydrolyzed under acidic (H+) or basic (OH−) conditions to produce diol-PBCD flame retardant 630. Diol-PBCD flame retardant 630 can then be bound to a polymer or prepolymer or reacted further to produce di-$L^1$-PBCD flame retardant 640. Formation of di-$L^1$-PBCD flame retardant 640 is discussed in greater detail with respect to FIG. 6A.

In process 600-3, CDT 310 is reacted with methanesulfonamide ($MeSO_2NH_2$), potassium osmate ($K_2[OsO_2(OH)_4]$), potassium carbonate ($K_2CO_3$), and catalytic hydroquinidine-2,5-diphenyl-4,6-pyrimidinediyl diether (cat. $(DHQD)_2Pyr$) in a water/tert-butyl alcohol ($H_2O$/tBuOH) solvent mixture. In a second step, p-toluenesulfonic acid (TsOH) is added to the reaction mixture. This results in the formation of a dimethyl dioxolane-CDD 670. The dimethyl dioxolane-CDD 670 is brominated in a $Br_2$/AcOH reaction to form a dimethyl dioxolane-PBCD compound 680. The dimethyl dioxolane moiety of compound 680 is hydrolyzed under acidic or basic conditions to produce diol-PBCD flame retardant 630. Diol-PBCD flame retardant 630 can then be bound to a polymer or prepolymer, or it can be reacted further to produce di-$L^1$-PBCD flame retardant 640.

Figure 7:
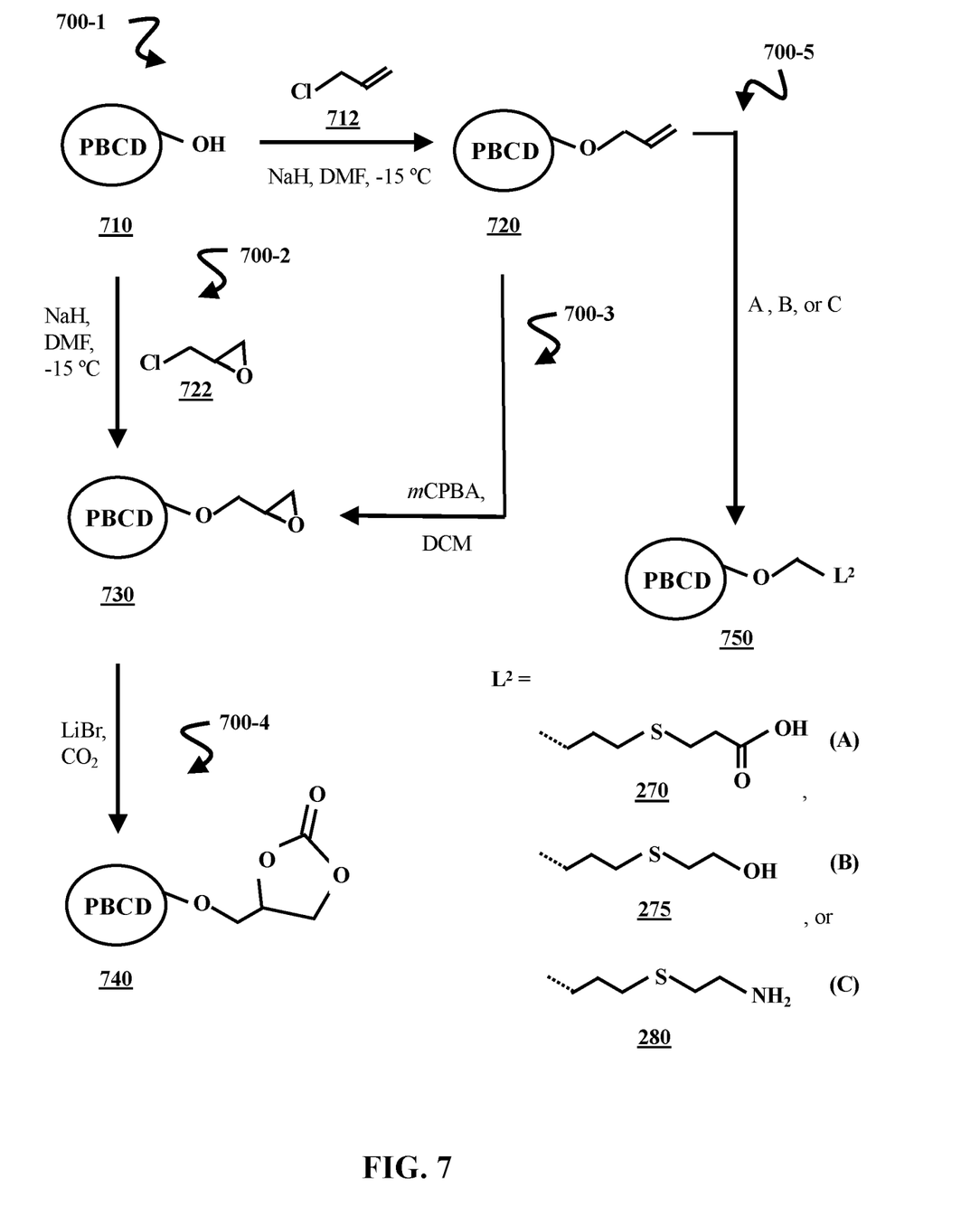
FIG. 7 is a chemical reaction diagram illustrating processes of modifying functionalized PBCD flame retardants, according to some embodiments of the present disclosure.

FIG. 7 is a chemical reaction diagram illustrating processes 700-1, 700-2, 700-3, 700-4, and 700-5 of modifying functionalized PBCD flame retardants, according to some embodiments of the present disclosure. In process 700-1, a brominated precursor 710 (e.g., hydroxy-functionalized PBCD flame retardant 340, 430, 540, 570, or 630) is reacted with allyl chloride 712. Allyl chloride 712 is a compound with a formula of $X-L^1$, where X is a chloro (—Cl) group and $L^1$ is an allyl 260 group. Carrying out this reaction in the presence of sodium hydride (NaH) and under low temperature conditions (e.g., approximately −15° C.) leads to the formation of an allyl-PBCD flame retardant 720 (e.g., functionalized PBCD flame retardant 350, 440, 580, 585, or 640, where $L^1$=allyl 260). A substantially similar low temperature reaction is carried out with the hydroxyl-PBCD flame retardant 710 and epichlorohydrin 722 ($X-L^1$, where X=Cl and $L^1$=epoxide 255) or in process 700-2. This reaction forms an epoxide-PBCD flame retardant 730 (e.g., functionalized PBCD flame retardant 350, 440, 580, 585, or 640, where $L^1$=epoxide 255). It should also be noted that allyl chloride 712 and epichlorohydrin 722 can be replaced by allyl bromide and/or epibromohydrin ($X-L^1$, where X=Br and $L^1$=allyl or epoxide, respectively) in some embodiments, though these analogous compounds are not illustrated in FIG. 3.

The epoxide-PBCD flame retardant 730 can also be derived from the allyl-PBCD flame retardant 720 in some embodiments. Addition of an oxygen atom donor to a compound having an alkene moiety can result in epoxidation of the alkenyl carbon-carbon double bond. For example, alkenes can be converted to epoxides by reactions with peroxide-containing compounds (e.g., peroxycarboxylic acids ($RC(O)O_2H$), hydrogen peroxide or alkyl peroxides in the presence of a metal catalyst, dimethyldioxirane, etc.). Therefore, under appropriate reaction conditions, an oxygen atom donor can be used to convert allyl-PBCD flame retardants 720 into epoxide-PBCD flame retardants 730. In process 700-3, the allyl-PBCD flame retardant 720 is reacted with a peroxycarboxylic acid (meta-chloroperoxybenzoic acid (mCPBA)) in dichloromethane (DCM) to produce the epoxide-PBCD flame retardant 730.

The epoxide-PBCD flame retardant 730 can be reacted further to form a propylene carbonate-PBCD flame retardant 740 ($L^2$=propylene carbonate 265). For example, in process 700-4 the epoxide-PBCD flame retardant 730 formed in process 700-2 or 700-3 is mixed with a solution containing lithium bromide (LiBr). Carbon dioxide ($CO_2$) is added to this reaction mixture, which causes conversion of the epoxide moiety to a propylene carbonate moiety, resulting in the propylene carbonate-PBCD flame retardant 740.

Alternative functional groups can be added to the PBCD flame retardant through reactions with allyl-PBCD flame retardants 720. For example, in process 700-5, thiols are reacted with allyl-PBCD flame retardant 720, resulting in the formation of thioether $L^2$ substituents with terminal functional groups. Process 700-5 includes a thiol-ene reaction between the allyl-PBCD flame retardant 720 and a thiol compound. The reaction produces $L^2$-functionalized PBCD flame retardants having substituents with thioether-linked $L^2$ functional groups. These compounds are referred to herein as thioether $L^2$-PBCD flame retardants 750. Depending on the selection of thiol compound, the thioether $L^2$ groups can have various reactive moieties (e.g., carboxylic acid (—COOH), hydroxyl (—OH), or amine (—$NH_2$) moieties).

Examples of thiol-ene reaction conditions that can be used to form thioether-linked $L^2$-PBCD flame retardants 750 in process 700-5 include reaction conditions A, B, and C.

Under reaction conditions A, the allyl-PBCD flame retardant 720 is reacted with 3-mercaptopropionate under UV light in a methanol (MeOH) solution. This reaction produces a carboxylic acid-functionalized thioether $L^2$-PBCD flame retardant 750 ($L^2$=thioether carboxylic acid 270). Under reaction conditions B, the allyl-PBCD flame retardant 720 is reacted with 2-mercaptoethanol under UV light, producing a hydroxy-functionalized thioether $L^2$-PBCD flame retardant 750 ($L^2$=thioether hydroxyl 275). Under reaction conditions C, the allyl-PBCD flame retardant 720 is reacted with cysteamine HCl in a methanol solution at approximately pH 9. This produces an amine-functionalized thioether $L^2$-PBCD flame retardant 750 ($L^2$=thioether amine 280).

The compounds described herein can contain one or more chiral centers. Unless otherwise noted, the disclosed structures cover all stereoisomers, conformers, rotamers, isomers, and enantiomers of the represented compounds. Further, polymers or other materials containing the disclosed compounds can include racemic forms of the compounds in addition to individual stereoisomers, as well as mixtures containing any of these. Substituents on the functionalized polybromocyclododecane flame-retardant compounds and other compounds described herein may participate in additional chemical reactions, transformations, or interactions, which can include synthesis, decomposition, single and/or double replacement, oxidation/reduction, acid/base, nucleophilic, electrophilic and radical substitutions, addition/elimination reactions, and polymerization reactions.

The synthetic processes discussed herein and their accompanying drawings are not to be construed as limiting. One skilled in the art would recognize that a variety of synthetic reactions may be used that vary in reaction conditions, components, methods, etc., which ultimately generate functionalized polybromocyclododecane flame-retardant compounds. In addition, the reaction conditions can optionally be changed over the course of a process. Further, in some embodiments, processes can be added or omitted while still remaining within the scope of the disclosure, as will be understood by a person of ordinary skill in the art.

Unless otherwise noted, chemical reactions are performed at ambient conditions or under slight heating with no special atmosphere or head space, and may be performed using standard organic solvents to manage mix properties such as viscosity and flow index. Standard procedures for quenching the reaction, solvent removal, and purification are performed. It should be noted that ranges (e.g., time, concentration, temperature, etc.) indicated herein include both endpoints and all numbers between the endpoints. Unless specified otherwise, the use of "about" or "approximately" in connection to a range applies to both ends of the range (e.g., "approximately 1 g-5 g" should be interpreted as "approximately 1 g-approximately 5 g").

What is claimed is:

1. A polybrominated flame-retardant compound, comprising:
   a cyclododecane moiety;
   at least two bromo groups; and
   at least one substituent having a reactive functional group selected from the group consisting of an allyl group, an epoxide, an acryloyl group, a methacryloyl group, a propylene carbonate group, an oxalate group, an amine group, and an amide group.

2. The polybrominated flame-retardant compound of claim 1, wherein the at least two bromo groups are bound to the cyclododecane moiety.

3. The polybrominated flame-retardant compound of claim 1, wherein at least one of the at least two bromo groups is bound to the at least one substituent.

4. The polybrominated flame-retardant compound of claim 1, wherein the at least one substituent includes the allyl group.

5. The polybrominated flame-retardant compound of claim 1, wherein the at least one substituent includes a thioether linker.

6. The polybrominated flame-retardant compound of claim 1, wherein the at least one substituent includes a benzyl moiety.

7. The polybrominated flame-retardant compound of claim 1, wherein the at least one substituent is linked to the cyclododecane moiety by an oxygen atom linker or an ester linker.

8. The polybrominated flame-retardant compound of claim 1, further comprising at least one additional substituent having a reactive functional group selected from the group consisting of a hydroxyl group, an epoxide group, a vinyl group, an acryloyl group, a methacryloyl group, a propylene carbonate group, an oxalate group, a carboxylic acid group, an amine group, and an amide group.

9. A process of forming a flame-retardant material, comprising:
   providing the polybrominated flame-retardant compound of claim 1; and
   incorporating the polybrominated flame-retardant compound into a polymer, wherein the incorporating includes covalent binding of the at least one reactive functional group to the polymer.

10. The process of claim 9, wherein the providing the the polybrominated flame-retardant compound comprises:
    selecting a substituent having the at least one reactive functional group;
    providing a compound having the selected substituent; and
    reacting the compound having the selected substituent with a brominated precursor, wherein the reaction causes the selected substituent to attach to the brominated precursor.

11. The process of claim 10, wherein the compound having the selected substituent is selected from the group consisting of a chloroacetate ester, a chloro-enone, 2-chloroacetamide, epichlorohydrin, and allyl chloride.

12. The process of claim 10, wherein the compound having the selected substituent is selected from the group consisting of a glycolic acid, a glycolate ester, a hydroxy-substituted enone, N-hydroxyacetamide, an acryloyl benzyl alcohol, methacryloyl benzyl alcohol, glycidol, and allyl alcohol.

13. The process of claim 10, wherein the brominated precursor includes at least two bromo groups and at least one hydroxyl group.

14. The process of claim 9, wherein the polymer is selected from the group consisting of a polystyrene, an epoxide resin, a polyhydroxyurethane, a polycarbonate, a polyester, a polyacrylate, a polyimide, a polyamide, a polyurea, and a poly(vinyl-ester).

15. An article of manufacture comprising a flame-retardant material, the flame-retardant material comprising:
    a polymer; and
    the polybrominated flame-retardant compound of claim 1 covalently bound to the polymer.

16. The article of manufacture of claim 15, wherein the polybrominated flame-retardant compound acts as a cross-linker in the polymer.

17. The article of manufacture of claim 15, wherein the polymer is selected from the group consisting of a polystyrene, an epoxide resin, a polyhydroxyurethane, a polycarbonate, a polyester, a polyacrylate, a polyimide, a polyamide, a polyurea, and a poly(vinyl-ester).

18. The article of manufacture of claim 15, further comprising an electronic component.

19. The article of manufacture of claim 15, further comprising a printed circuit board.

20. The article of manufacture of claim 15, wherein the polybrominated flame-retardant compound includes a cyclododecane moiety with four bromo groups.

* * * * *